US005622764A

United States Patent [19]

Battles

[11] Patent Number: 5,622,764

[45] Date of Patent: Apr. 22, 1997

[54] STERILIZATION INDICATORS AND METHODS

[75] Inventor: Donald R. Battles, Arden Hills, Minn.

[73] Assignee: Minnesota Mining and Manufacturing Company, St. Paul, Minn.

[21] Appl. No.: 477,543

[22] Filed: Jun. 7, 1995

[51] Int. Cl.[6] .............................. B32B 3/00; B32B 3/10; B32B 7/08

[52] U.S. Cl. .......................... 428/52; 428/41.5; 428/42.2; 428/53; 428/54; 428/58; 428/131; 428/132; 428/138; 428/351; 428/355 R

[58] Field of Search ................................ 428/52, 53, 54, 428/58, 131, 132, 138, 351, 355, 41.5, 42.2

[56] References Cited

U.S. PATENT DOCUMENTS

| | | | |
|---|---|---|---|
| 2,838,421 | 6/1958 | Sohl | 117/122 |
| 2,889,799 | 6/1959 | Korpman | 116/114 |
| 3,067,057 | 12/1962 | Dabroski | 117/68.5 |
| 3,078,182 | 2/1963 | Crone, Jr. et al. | 117/68.5 |
| 3,096,202 | 7/1963 | De Groot Von Arx | 117/68.5 |
| 3,098,754 | 7/1963 | Dixon | 106/88 |
| 3,152,940 | 10/1964 | Abel et al. | 156/157 |
| 3,258,312 | 6/1966 | Olson | 23/232 |
| 3,311,084 | 3/1967 | Edenbaum | 116/114 |
| 3,360,337 | 12/1967 | Edenbaum | 23/253 |
| 3,360,338 | 12/1967 | Edenbaum | 23/253 |
| 3,360,339 | 12/1967 | Edenbaum | 23/253 |
| 3,386,807 | 6/1968 | Edenbaum | 23/253 |
| 3,441,430 | 4/1969 | Peterson | 117/68.5 |
| 3,523,011 | 8/1970 | Bhiwandker et al. | 23/253 |
| 3,627,469 | 12/1971 | Cheng | 23/232 R |
| 3,667,916 | 6/1972 | Sliva et al. | 23/230 R |
| 3,763,117 | 10/1973 | McKenna, Jr. et al. | 260/78.5 E |
| 3,852,034 | 12/1974 | Gunther | 23/232 R |
| 3,862,824 | 1/1975 | Chapman | 23/253 TP |
| 3,865,770 | 2/1975 | Blake | 260/27 R |
| 3,873,018 | 3/1975 | Donnay | 428/54 |
| 3,890,292 | 6/1975 | Bohme et al. | 260/80.76 |
| 4,015,937 | 4/1977 | Miyamoto et al. | 23/230 R |
| 4,094,642 | 6/1978 | Sumimoto et al. | 23/254 R |
| 4,168,779 | 9/1979 | Yokokoji et al. | 206/439 |
| 4,188,437 | 2/1980 | Rohowetz | 428/199 |
| 4,341,680 | 7/1982 | Hauber et al. | 525/329 |
| 4,342,063 | 7/1982 | Thornell | 361/79 |
| 4,388,432 | 6/1983 | Eskay | 524/388 |
| 4,413,080 | 11/1983 | Blake | 524/187 |
| 4,447,482 | 5/1984 | Heinzelman et al. | 428/352 |
| 4,562,102 | 12/1985 | Rabuse et al. | 428/54 |
| 4,563,379 | 1/1986 | Krüger | 428/58 |
| 4,569,960 | 2/1986 | Blake | 524/145 |
| 4,865,669 | 9/1989 | Schmidt | 428/58 |
| 4,898,762 | 2/1990 | Brown et al. | 428/152 |
| 5,064,576 | 11/1991 | Suto | 252/962 |
| 5,125,995 | 6/1992 | D'Haese et al. | 156/155 |
| 5,397,614 | 3/1995 | Patnode et al. | 428/40 |
| 5,512,612 | 4/1996 | Brown et al. | 523/218 |

FOREIGN PATENT DOCUMENTS

| | | |
|---|---|---|
| 0282178 | 9/1988 | European Pat. Off. . |
| 0297451 | 1/1989 | European Pat. Off. . |
| 0352442 | 1/1990 | European Pat. Off. . |
| 1370470 | 10/1974 | United Kingdom . |
| 1458553 | 12/1976 | United Kingdom . |

*Primary Examiner*—Terrel Morris
*Attorney, Agent, or Firm*—Gary L. Griswold; Walter N. Kirn; F. Andrew Ubel

[57] ABSTRACT

Sterilization indicators utilizing moisture-resistant, water-dispersible, pressure sensitive adhesives are provided. The sterilization indicators comprise at least one backing strip, preferably water-dispersible, which is coated on at least one side with the moisture-resistant, water-dispersible, pressure sensitive adhesive. A sterilization indicator strip is affixed to the backing strip and is easily removable from the sterilization indicator. The indicator tapes are useful to maintain a sterilization wrapper containing articles to be sterilized in a closed position during sterilization, and normal pre- and post-sterilization handling, while also providing a means to indicate if the wrapped articles have passed through a sterilization cycle. After use, the sterilization indicator strip is easily removed, and the adhesives coating the sterilization indicators, and preferably also the backing strips, disperse an aqueous alkali solution, such as are found in commercial laundries. Methods of making and using the sterilization indicators are also provided.

14 Claims, 1 Drawing Sheet

32 36 38 36 30 34 32 33

STERILIZATION INDICATORS AND METHODS

FIELD

This invention relates to sterilization indicators, and more particularly to sterilization indicator tapes utilizing water-dispersible pressure sensitive adhesives, for closure of reusable wrappers in which a sterilization indicator strip is easily removable from the sterilization indicator, and to methods of using the same.

BACKGROUND

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are packaged in cloth sterilization wrappers and the wrapped package is then sterilized and stored for subsequent use. As may be apparent, there is a potential danger in such a procedure. There is a prospect of unsterilized packages becoming mixed with sterilized packages when stored for use.

To prevent unsterilized products from being used by the physician or attendant, various types of sterility indicators have been developed which are attached to, or incorporated into, the wrapped sterilization package. This permits a user to immediately determine whether a particular package has been passed through the sterilizer. Such sterilization indicators have, in many instances, been placed in the wrapped package or attached to the wrapped package. The most convenient way of applying such sterilization indicators, however, is to have the indicator carried by pressure sensitive adhesive indicator tapes used for holding the cloth wrapper in a closed position prior to, during, and after sterilization of the enclosed products.

Various pressure sensitive adhesives have been used with tape backings that include appropriate color changing means to indicate if the package has been exposed to sterilization conditions. Examples of pressure sensitive adhesives employed with such indicator tapes include water insoluble natural rubber-based adhesives, natural rubber and synthetic rubber blend adhesives, styrene-isoprene-styrene block copolymers with tackifying resins, vinyl ethers, and high molecular weight acrylate copolymers having minimal amounts of plasticizing monomers included therein. See e.g., U.S. Pat. Nos. 2,889,799, 3,067,057, 3,078,182, 3,311,084, and 4,188,437. Typically, these indicator tapes use a paper, fabric or film backing, and an adhesive chemistry that is resistant to softening upon exposure to sterilization conditions (including heat, steam or other chemical methods).

Cloth sterilization wrappers may be disposed of or retained after use. If retained, the soiled cloth wrappers must be cleaned, usually by laundering in soapy water, such as an aqueous alkali solution. These wrappers will then be reused. The expense of some cloth wrappers, such as treated synthetic wrappers and untreated wrappers, demands that the closure and sterilization indicator tapes not damage the wrapper after use.

The various indicator tapes referenced above are not formulated to disperse during cleaning, and in fact, if not manually removed before laundering, may permanently damage a sterilization wrapper. Specifically, the heat and chemicals associated with laundering and drying of the sterilization wrappers will cause the pressure sensitive adhesives used with the indicator tapes to transfer into the fabric of the cloth wrappers, and thereby permanently damage the sterilization wrapper.

In addition, in the various indicator tapes referenced above, there is the potential that the sterilization indicating portion of the indicator tape, which typically contains heavy metals, will be discharged into the waste stream if not removed before laundering.

Water-dispersible pressure sensitive adhesives have been made and used for paper making and printing operations which require splicing of the end of one row of paper to the beginning of another row. For example, U.S. Pat. Nos. 3,865,770, 4,413,080, 4,569,960, 3,441,430, and 2,838,421 disclose such water-dispersible pressure sensitive adhesives and/or splicing tapes made therefrom. Further examples of water-soluble or water-dispersible pressure sensitive adhesive compositions and/or tapes made therefrom can be found in U.S. Pat. Nos. 4,413,082, 4,341,680, 4,388,432, 3,890,292, 3,763,117, 3,152,940, 3,096,202, and European Patent Publication Nos. 0 352 442 and 0 297 451. In addition, U.S. patent application No. 07/580,116 describes an autoclavable water-dispersible pressure sensitive adhesive on a dispersible backing for use as a means to adhere cloth to cloth or cloth to skin in areas where high amounts of fluid would be present.

U.S. patent application Nos. 07/889,647 and 08/257,947 provide a sterilization indicator tape which utilizes a water-dispersible, pressure sensitive adhesive. These indicator tapes include a non-water-dispersible backing which includes thereon a sterilization indicator, and a moisture resistant, water-dispersible, pressure sensitive adhesive coating on at least one of two opposing sides of the non-water-dispersible backing. Such a construction permits laundering of sterilization wrappers without having to remove the indicator tape prior to laundering. The tapes are capable of maintaining a wrapped bundle of articles in a closed position during sterilization, and normal pre- and post-sterilization handling. The water-dispersible, pressure sensitive adhesive on the indicator tapes, however, will disperse upon immersion in the aqueous alkali laundering solutions during laundering, while the tape backing containing the sterilization indicator, such as an indicator ink, stays in tact. Although this type of sterilization indicator tape permits laundering of sterilization wrappers without removal of the indicator tape, the sterilization indicator material (typically containing heavy metals) is introduced into the laundering process and potentially into the waste stream. The non-water-dispersible backing containing the sterilization indicator portion remains intact, and must be collected from laundering equipment following the laundering procedure. Following laundering, the tape can be collected, and disposed.

To date, no indicator tapes utilizing an indicator portion which is easily removable prior to laundering of a sterilization wrapper exist. Thus, present indicator tapes containing sterilization indicator portions, must be collected from industrial laundering equipment following the laundering of sterilization wrappers.

SUMMARY

The present invention provides a solution to the problems presented by sterilization indicator tapes known in the art. The sterilization indicator of the present invention is capable of maintaining a wrapped bundle of articles in a closed position during sterilization, and normal pre- and post-sterilization handling, but the sterilization indicating portion of the indicator tape is easily removable from the sterilization wrapper prior to laundering of the wrapper. In preferred embodiments, the present invention provides a sterilization indicator in which the portion remaining after removal of the sterilization indicating portion completely disperses upon laundering, thereby eliminating the need to collect any material after laundering. Easy removal of the sterilization indicator portion of a sterilization indicator tape prior to laundering means that the indicator portion, which typically contains heavy metals, will not be introduced into the laundering process of the used sterilization wrapper, and thereby eliminates the potential that the sterilization indicator portion of the indicator tape will be discharged into the waste stream.

The present invention provides a sterilization indicator which includes at least one backing strip having opposing sides and a moisture resistant, water-dispersible, pressure sensitive adhesive on at least one of the opposing sides of the backing strip. A sterilization indicator strip is affixed to the backing strip or strips such that the sterilization indicator strip may easily be removed from the sterilization indicator. The backing strips preferably are water-dispersible, but may be non-water-dispersible.

The sterilization indicators of the present invention may have any of several preferred configurations. In one embodiment, two backing strips are provided and a sterilization indicator strip is affixed to an end of each of the two backing strips. In another embodiment, one backing strip is provided and a sterilization indicator strip is affixed to an end of the backing strip. In yet another embodiment, a backing strip is provided which has one or more apertures. The apertures may be generally in the middle of the backing strip or near an end of the backing strip. A sterilization indicator strip is affixed to a side of the backing strip having the moisture-resistant, water-dispersible, pressure sensitive adhesive such that the sterilization indicator strip is viewable through the aperture or apertures in the backing strip.

The sterilization indicator strip preferably comprises an indicator ink in combination with a binder printed onto a non-water dispersible backing, the indicator ink being capable of undergoing a color change when exposed to sterilization conditions. The sterilization indicator strip may be affixed to the backing strip or strips by adhering the sterilization indicator strip or a portion or portions thereof to the side of the backing strip or strips having the moisture resistant, water-dispersible, pressure sensitive adhesive.

The backing strip utilized in the sterilization indicator of the present invention may be water-dispersible or non-water-dispersible. In embodiments of the claimed invention in which the backing strips are non-water-dispersible, such backing strips may include a woven backing, a non-woven backing, a cloth backing, a film backing, a paper backing, a foil backing, or combinations thereof.

The indicator ink utilized in the sterilization indicator strip may be a steam sterilization indicator ink, an ethylene-oxide sterilization indicator ink, or combinations thereof. In a preferred embodiment, a lead carbonate-sulfur sterilization indicator ink is utilized. In preferred embodiments, the binder utilized in the sterilization indicator strip of the present invention is an acrylate binder.

In preferred embodiments of the present invention, the moisture-resistant, water-dispersible, pressure sensitive adhesive is a composition which is dispersible at an alkaline pH but not at an acidic or neutral pH. Preferably the adhesive contains a polymer formed from A, B, and C monomers and less than about 0.1 parts plasticizer per part polymer.

The "A" monomer is preferably a hydrophobic monomer selected from the group consisting of an acrylic or a methacrylic ester of a non-tertiary alcohol having from 2 to 14 carbon atoms. Preferably the "A" monomer comprises from 50 to 80% by weight of the polymer.

The "B" monomer is preferably a monomer selected from the group consisting of β-carboxyethylacrylate, the salt of β-carboxyethylacrylate, vinyl carboxylic acid, the salt of vinyl carboxylic acid, and mixtures thereof. Preferably the "B" monomer comprises from 10 to 30% by weight of the polymer, and the carboxylic acid groups of the polymer are neutralized with from about 0.5 to about 2 equivalents of an alkali metal hydroxide per carboxylic acid group. When the "B" monomer comprises a mixture of β-carboxyethylacrylate and vinyl carboxylic acid, the β-carboxyethylacrylate preferably comprises at least 10% by weight of said polymer.

The "C" monomer is preferably a water-dispersible macromolecular monomer which has the formula X-Y-Z. "X" is a moiety copolymerizable with "A" and "B"; "Y" is a divalent linking group which joins "X" to "Z"; and "Z" is a water-dispersible group which contains at least two units which are essentially unreactive under the free radical initiated copolymerization conditions used to form the polymer. Preferably the "C" monomer comprises from 10 to 30% by weight of said polymer.

The sterilization indicators of the present invention are capable of maintaining a wrapped bundle of articles in a closed position during sterilization and normal pre- and post-sterilization handling. The pressure sensitive adhesive exhibits sufficient adhesion to maintain the wrapped bundle of articles in the closed position during sterilization and normal pre- and post-sterilization handling. The backing strip or strips utilized in the present invention exhibit sufficient strength that they will not tear during sterilization and normal pre- and post-sterilization handling.

In the sterilization indicators of the present invention, the sterilization indicator strip is easily removable prior to laundering. Because there is preferably no adhesive on the sterilization indicator strip, it may be easily torn away from the remainder of the sterilization indicator prior to laundering. The sterilization indicator strip will not be introduced into the laundering process and therefore has no potential of entering the waste stream. If, as is preferred, a water-dispersible backing strip is used, the backing strip or strips left on a sterilization wrapper before laundering will completely disperse during laundering, eliminating the need to collect material from laundering equipment after laundering.

In embodiments of the present invention where the sterilization indicator strip is affixed to an end of one or more backing strips, the backing strips may be perforated at or near the end to which said sterilization indicator strip is affixed. In embodiments of the present invention where the sterilization indicator strip is affixed to a backing strip having apertures therethrough, the backing strip may be perforated near the sterilization indicator strip. Such perforation permits even easier removal of the sterilization indicator strip prior to laundering the wrapper.

The invention also provides a method of making a sterilization indicator which includes the following steps: providing at least one backing strip having ends and opposing sides, and a sterilization indicator strip which includes an indicator ink in combination with a binder printed onto a backing; coating a moisture resistant, water-dispersible, pressure sensitive adhesive on one of the opposing sides of the backing strip or strips; and affixing the sterilization indicator strip to an end of the backing strip or strips. In preferred embodiments, the method may further comprise a step of perforating the backing strip or strips near the end of the backing strip to which the sterilization indicator strip is affixed.

The present invention also provides a method for making a sterilization indicator which includes the steps of providing a backing strip having ends and opposing sides and further having at least one aperture through the backing strip, and a sterilization indicator strip which includes an indicator ink in combination with a binder printed onto a backing; coating a moisture resistant, water-dispersible, pressure sensitive adhesive on one of the opposing sides of the backing; and affixing the sterilization indicator strip to the backing strip such that the sterilization indicator strip is viewable through the aperture or apertures.

Finally, the present invention provides a method of using a sterilization indicator as a wrapper closure including the following steps: providing an indicator which includes at least one backing strip having opposing sides, and a moisture resistant, water-dispersible, pressure sensitive adhesive coated on one of the opposing sides of the backing strip, the backing strip having a sterilization indicator strip affixed thereto; applying the indicator to a sterilization wrapper containing a bundle of articles such that the bundle will remain substantially closed during sterilization and normal pre- and post-sterilization handling. The method of using the sterilization indicator as a wrapper may further comprise removing the sterilization indicator strip from the sterilization wrapper prior to laundering the wrapper. In preferred embodiments, the backing strip is perforated, permitting easy removable prior to laundering of the sterilization wrapper.

DEFINITIONS

For the purposes of this invention:

"Normal and pre- and post-sterilization handling" refers to handling of wrapped bundles or packs that would likely occur in the day-to-day operation of hospitals, clinics, laundries, and the like. This can include loading of packs into and out of sterilizers, placement of packs into storage, and movement of packs throughout and in between institutions.

"Sterilization wrapper" or "wrapper" refers to a covering, typically made of cloth, used to wrap an item or items to be sterilized by steam, gas, etc., and in fact may be formed by the outer side of an item to be sterilized. Preferably, but not necessarily, the sterilization wrapper is reusable. Cloth is defined in its broadest sense to be fabric or material formed by weaving, knitting, knotting, pressing, bonding, crocheting, interlocking, interlacing, melt-blowing, or felting of natural or synthetic yarns, filaments, or fibers. Non-limiting examples of cloth include woven, knitted, or non-woven fabrics and webs, used as sterilization wrappers.

BRIEF DESCRIPTION OF THE DRAWINGS

The invention may be further illustrated by reference to the accompanying drawings wherein.

DETAILED DESCRIPTION

FIGS. 1*a*–1*d* illustrate preferred embodiments of the sterilization indicator according to the present invention.

Figure 1A:
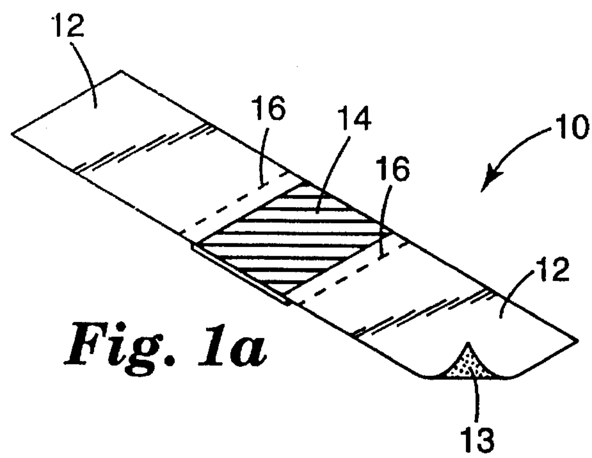
FIGS. 1*a*–1*d* are perspective views of various embodiments of the sterilization indicator according to the present invention.

Referring to FIG. 1*a*, two backing strips 12 each have opposing sides and a moisture resistant, water-dispersible, pressure sensitive adhesive 13 on at least one of the opposing sides. Preferably, backing strips 12 are water-dispersible, but may also be non-water-dispersible. Sterilization indicator strip 14 is affixed to an end of each of the backing strips 12. Sterilization indicator strip 14 is preferably affixed to an end of each of the backing strips 12 by adhering the sterilization indicator strip 14 to a side of the backing strip 12 having the moisture resistant, water-dispersible, pressure sensitive adhesive coated thereon.

The sterilization indicator strip 14 preferably includes a sterilization indicator ink in combination with a binder printed on to a non-water-dispersible backing. The indicator ink is capable of undergoing a color change when exposed to sterilization conditions. While the sterilization indicator 14 is shown printed in a diagonal pattern in FIG. 1*a*, it will be appreciated that any pattern, and/or variations in total surface area covered, could be encompassed by the printed sterilization indictor strip 14. Optionally, and preferably, perforations 16 may be provided in the backing strips 12 at or near the ends of the backing strips 12 to which the sterilization indicator strip is affixed. The perforations 16 permit easy removal of the sterilization indicator strip from the sterilization indicator 10 prior to laundering of a sterilization wrapper bundled with the sterilization indicator of the present invention.

Figure 1B:
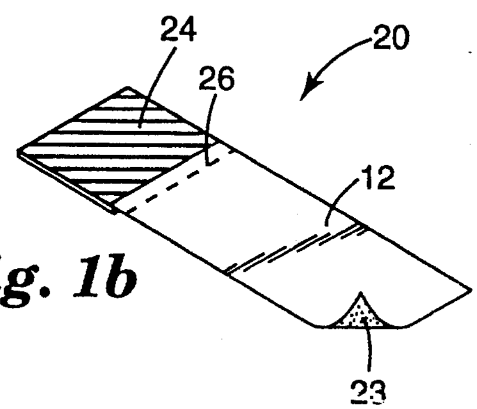

FIG. 1*b* shows another preferred embodiment of the sterilization indicator 20 of the present invention. In this embodiment, a single backing strip 22 having a moisture resistant, water-dispersible, pressure sensitive adhesive 23 thereon is provided which is similar to the backing strips described with reference to FIG. 1*a*. A sterilization indicator strip 24 is affixed to an end of the backing strip 22 in a manner similar to that described with reference to FIG. 1*a*. Perforations 26 optionally may be provided on the backing strip 22 at or near the end to which the sterilization indicator strip is affixed, to ease removal.

Figure 1C:
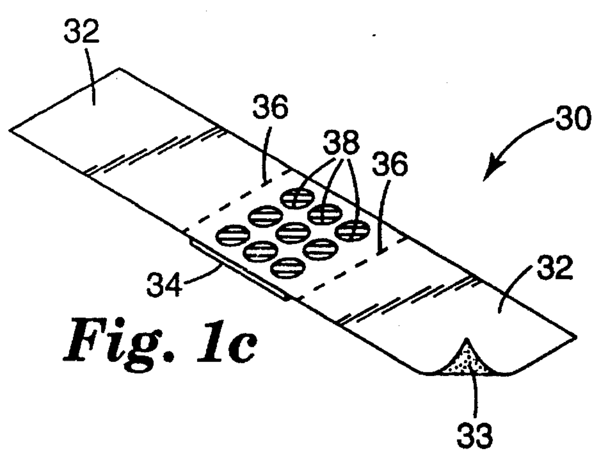
Figure 1D:
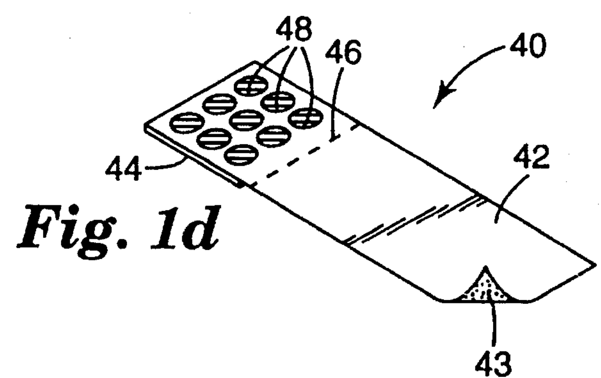

FIG. 1*c* shows another preferred embodiment of the sterilization indicator 30 of the present invention. A backing strip 32 similar in construction to the backing strips described above with reference to FIGS. 1*a* and 1*b* is provided. The backing strip 32 has one or more apertures 38. While the backing strip 32 shown in FIG. 1*c* shows a plurality of apertures, it will be appreciated that backing strip 32 may be provided with a single aperture or a plurality of apertures. A sterilization indicator strip 34 similar to that described above with reference to FIGS. 1*a* and 1*b* is affixed to a side of backing strip 32 having the moisture resistant, water-dispersible, pressure sensitive adhesive 33 thereon. Sterilization indicator strip 34 is affixed to the backing strip 32 such that the sterilization indicator strip 34 is viewable through the aperture or apertures 38 in backing strip 32. Perforations 36 optionally may be provided in backing strip 32 near ends of sterilization indicator strip 34 to permit easy removal of sterilization indicator strip 34.

FIG. **1*d* shows still another preferred embodiment of the sterilization indicator 40 of the present invention. In this embodiment, a backing strip 42 is provided having an aperture or apertures 48 near an end of the backing strip 42. A sterilization indicator strip 44 is affixed to a side of the backing strip 42 having the moisture resistant, water-dispersible, pressure sensitive adhesive 43 thereon. Sterilization indicator strip 44 is affixed to backing strip 42 such that the sterilization indicator strip 44 is viewable through the aperture or apertures 48 in backing strip 42. Perforation 46 may be provided to permit easy removal of sterilization indicator strip 44** from the sterilization indicator.

The sterilization indicators of the present invention utilize a moisture resistant, water-dispersible, pressure sensitive adhesive on at least one side of the backing strip. In this regard, it is preferred that the water-dispersible adhesive comprise an acrylate-based adhesive copolymer.

In a preferred embodiment, the acrylate-based adhesive copolymer is comprised of three monomers, "A", "B", and "C", and less than about 0.1 parts plasticizer per part polymer. "A" preferably is a hydrophobic monomer selected from the group consisting of an acrylic or a methacrylic ester of a non-tertiary alcohol having between 2 to 14 carbon atoms. In preferred embodiments, monomer A comprises from about 50 to about 80% by weight of the polymer. Of the acrylic acid esters of non-tertiary alkyl alcohols, butyl acrylate is preferred.

Monomer B preferably is selected from the group consisting of beta-carboxyethylacrylate or the salt of β-carboxyethylacrylate, vinyl carboxylic acid, the salt of vinyl carboxylic acid, and mixtures thereof. Preferably monomer B comprises from 10 to 30% by weight of the polymer. The carboxylic acid groups of the polymer are neutralized with from about 0.5 to about 2 equivalents of an alkali metal hydroxide per carboxylic acid group. When the B monomer comprises a mixture of beta-carboxyethylacrylate and vinyl carboxylic acid, the beta-carboxyethylacrylate preferably comprises at least 10% by weight of the polymer.

Monomer C preferably is a water-dispersible, macromolecular monomer which has the formula X-Y-Z. "X" is a moiety copolymerizable with A and B; "Y" is a divalent linking group which joins X to "Z"; and Z is a water-dispersible group which contains at least two units which are essentially unreactive under the free radical initiated copolymerization conditions used to form the polymer. Preferably monomer C comprises from 10 to 30% by weight of the polymer.

The preferred moisture resistant, water-dispersible, pressure sensitive adhesives for use in the sterilization indicators of the present invention, and methods of preparing such adhesives are fully described and set forth in U.S. Pat. No. 5,397,614, assigned to 3M, the entire disclosure of which is herein incorporated by reference.

The backing strips utilized in the sterilization indicators of the present invention are preferably water-dispersible backings. Water-dispersible backings may include those materials that are totally soluble in water or alkali, as well as materials that break apart into small particles or fibers that are capable of being supported in a liquid medium. Totally soluble materials include, but are not limited to, water soluble polymers such as poly(vinyl alcohol) of various degrees of hydrolysis, or alkali soluble polymers such as those available from Belland AG, Biberist, Switzerland. Materials that will disperse into fibers or particles capable of being washed away with a waste water stream include untreated papers or tissues, such as those papers identified as crystex tissue from Crystal Paper Co., or untreated bond tablet paper from International Paper (Springhill Form Bond MP 3800). Untreated creped Kraft papers such as 47.2 kg/m$^2$ basis weight paper from Mosinee Corporation, Mosinee, Wis. also possesses the desired attributes of dispersibility upon agitation and laundering. Combinations of these materials could also be used, e.g., papers sized with poly(vinyl alcohol).

The backing strips may also be non-water-dispersible. Non-water-dispersible backings can be made from any non-water-dispersible film, paper, or other sheet material physically capable of withstanding the conditions of a given steam and/or ethyleneoxide sterilization cycle. Non-limiting examples of other suitable backings include polymeric backings such as polyolefin-based film backings (e.g., polyethylene backings, polyester backings, and isotactic polypropolene backings such as disclosed in U.S. Pat. No. 4,898,762, the disclosure of which is herein incorporated by reference); as well as latex-saturated paper backings; foil backings; woven backings; and non-woven backings. Non-water-dispersible backings could also include papers treated with binders and/or wet-strength additives to render the backing non-water-dispersible.

Sterilization indicator strips of the present invention preferably comprise an indicator ink in combination with a binder printed onto a non-water-dispersible backing. Suitable non-water-dispersible backings for the preferred sterilization indicator strip include the non-water-dispersible backings described above. The backing of the sterilization indicator strip is coated with an ink capable of changing color upon exposure to the given conditions of a sterilization cycle. Virtually any indicator ink can be used with the backings of the sterilization indicator strips in the present invention, as long as the ink and adhesive components do not react to cause premature color development of the indicator ink in areas of adhesion between the sterilization indicator strip and the backing strips. Thus, steam sterilization indicator inks, such as lead carbonate-sulfur indicator inks, ethyleneoxide sterilization indicator inks, or both types of indicator inks, can be imprinted on the non-water-dispersible backing. See, e.g., U.S. Pat. No. 3,667,916, the disclosure of which is herein incorporated by reference. Non-limiting examples of suitable inks according to the present invention are disclosed in U.S. Pat. Nos. 3,386,807; 3,098,754; 3,360,337; 3,360,338; 3,360,339; 3,862,824; 3,523,011; 4,382,063; 3,258,312; 3,627,469; 3,852,034; 4,015,937; 4,094,642; 4,168,779; 5,064,576; UK Patent Nos. 1 458 553, and 1 370 470; and EPO Publication No. 0 282 178, the disclosures of which are all herein incorporated by reference.

The preferred ink for a steam sterilizer is a lead carbonate-sulfur system in a binder system, Gravure printed in lines onto the Kraft paper backing. Preferably, the ink system comprises 38% binder, 23% sulfur, 15% lacquer thinner, 23% lead carbonate, and 1% clay (available as "BENTONE" 38, LM Chemicals, Hightstown, N.J.).

Virtually any binder can be utilized with the indicator inks of the present invention, as long as the binder is capable of maintaining the utilized ink on the backing during laundering. Thus, the binder and ink must be compatible. The preferred binder system is 24% nitrocellulose ethylalcohol (Hercules Inc., Wilmington, Del.); 3% phenol-formaldehyde resin (BECKCITE™ 24-102, BTL Specialty Resins, Toledo, Ohio); 9% tricresol phosphate; 14% butylalcohol; 27% xylene and 23% butylacetate.

The ink printed Kraft paper is then strengthened using a vulcanized natural rubber-wood rosin system coated on to the paper. Preferably, the rubber system comprises 23% natural rubber (Goodyear Tire & Rubber Co., Akron, Ohio); 6% zincoxide (Sherwin Williams, Cleveland, Ohio); 3% titaniumdioxide (Type A-140, New Jersey Zinc Co., Palmerton, Pa.); 29% wood-rosin (TENEX™ 36-710, Reichold Chemicals Inc., Oakbrook, Ill.); 2% calcium lithol pigment (Hercules Inc., Wilmington, Del.); and 37% mineral spirits. The preferred vulcanizer used to cross-link the rubber system is 40% white mineral oil (Type #31 USP; AMOCO Chemical Corp., Chicago, Ill.); 15% tetramethylthirum disulfide accelerator (RT Vanderbilt Co., Norwalk, Conn.); and 45% ortho-pentamethylenethiuram sulfads (RT Vanderbilt Co.).

The printed sterilization indicator strip is then treated to decrease moisture penetration of the paper. Preferably an acrylate polymer solution is utilized. The preferred solution is 19% butylalcohol, 0.2% phosphoric acid, 9% urea, 0.8% aqueous ammonia, 31% formaldehyde, 6% isopropyl alcohol, 10% acrylic polymer (ELVACITE™ 2044; E I. DuPont Nemours, Wilmington, Del.); 9% butanol and 15% xylene.

The tapes are preferably manufactured on tape rolls for continuous feeding for application to cloth sterilization wrappers.

The construction of the sterilization indicators of the present invention permits easy removal of the sterilization indicator strip from a sterilization wrapper prior to laundering of a used sterilization wrapper. This advantage is achieved by affixing the sterilization indicator strip to the backing strip such that it may easily be removed prior to laundering. The sterilization indictor strip, which does not contain an adhesive coated thereon, may easily be torn away prior to laundering. In preferred embodiments where perforations are provided, removal of the sterilization indicator strip is made even easier.

The sterilization indicators of the present invention serve strictly as an indicator that a wrapped package has been sterilized, e.g., by attachment of the sterilization indicator to the outside of the wrapped package. However, it is preferred that the sterilization indicators of the present invention serve a dual purpose. Specifically, it is preferred that the indicator tapes be used to hold the wrapped package in a closed position, and also provide a means to indicate completion of a sterilization cycle. Whether utilized for a single or dual purpose, the water-dispersible, pressure sensitive adhesives utilized on the sterilization indicator backing strips of the present invention disperse when immersed in aqueous alkali solutions in less than about 40–60 minutes. In preferred embodiments of the present invention where a water-dispersible backing strip is utilized, the backing strip will also disperse under these laundering conditions. Since the sterilization indicator strip has been removed prior to laundering, nothing is left to collect from the laundering equipment. Where a non-dispersible backing strip or strips are utilized, the non-dispersible backing strips remain intact following the laundering cycle, and can be collected in the laundering equipment after laundering. In both embodiments, the dispersion of the adhesive causes the sterilization indicator to separate from the laundered sterilization wrapper. There is no damage to the wrapper caused by, for example, adhesive residue, which damage would necessitate premature discarding of the wrapper. In addition, potentially contaminating sterilization indicator strips are not introduced into the laundering cycle and thus have no potential of being discharged into the waste stream. The backing strips either disperse or are collected, leaving no damage to the garments or the environment.

Furthermore, the water-dispersible, pressure sensitive adhesive utilized on the sterilization indicators of the present invention resist moisture and heat generated during use as a sterilization wrapper closure, and thereby avoid loss of adhesion at the time of sterilization. Even if some transfer of the adhesive into the wrapper fabric occurs, the dispersability of the adhesive ensures that the wrapper will not suffer any permanent damage.

Yet another advantage of the invention is that the sterilization indicators reduce the time for processing goods to be laundered. Specifically, inspection for sterilization tape or adhesive residue does not need to take place since the pressure sensitive adhesive will disperse in the cleaning cycle.

Yet a further advantage of the invention is that the water-dispersible, pressure sensitive adhesive indicator tape is tamper-evident. Once the tape is peeled from a sterilized wrapper it cannot be re-adhered because the adhesive remains on the wrapper, thus indicating that sterility has been compromised.

While description of preferred embodiments and parameters of the present invention is provided herein, it will be appreciated that the scope of the invention is not limited thereto and that other embodiments of the present invention are within the scope of the appended claims. Reference is made to the following claims for an understanding of the scope of the present invention.

What is claimed is:

1. A sterilization indicator, comprising:

two backing strips, each of said backing strips having ends and opposing sides and a moisture-resistant, water-dispersible, pressure sensitive adhesive on at least one of said opposing sides; and a sterilization indicator strip affixed to an end of each of said backing strips such that said sterilization indicator strip is easily removable from the backing strips prior to laundering and said sterilization indicator strip comprises an indicator ink in combination with a backing, wherein said indicator ink is capable of undergoing a color change when exposed to sterilization conditions.

2. The indicator of claim 1, wherein said backing strips are water-dispersible.

3. The indicator of claim 1, wherein said backing strips are non-water-dispersible.

4. The indicator of claim 3, wherein said backing strips are selected from the group consisting of woven backings, non-woven backings, cloth backings, film backings, paper backings, and foil backings.

5. The indicator of claim 1, wherein said indicator ink is selected from the group consisting of steam sterilization indicator inks, ethylene oxide sterilization indicator inks, or a combination of a steam sterilization indicator ink and an ethylene oxide sterilization indicator ink.

6. The indicator of claim 5, wherein said steam sterilization indictor ink comprises a lead carbonate-sulfur indicator ink.

7. The indicator of claim 1, wherein said binder comprises an acrylate binder.

8. The indicator of claim 1, wherein said moisture resistant, water-dispersible, pressure sensitive adhesive comprises a composition which is dispersible at an alkaline pH but not at an acidic or neutral pH, comprising:

a polymer formed from A, B, and C monomers wherein

A is a hydrophobic monomer selected from the group consisting of an acrylic or a methacrylic ester of a non-tertiary alcohol having from 2 to 14 carbon atoms, wherein A comprises from 50 to 80% by weight of said polymer, B is a monomer selected from the group consisting of β-carboxyethylacrylate, the salt of β-carboxyethylacrylate, vinyl carboxylic acid, the salt of vinyl carboxylic acid, and mixtures thereof, wherein B comprises from 10 to 30% by weight of said polymer, wherein the carboxylic acid groups of said polymer have been neutralized with from about 0.5 to about 2 equivalents of an alkali metal hydroxide per carboxylic acid group, and wherein when the mixture of β-carboxyethylacrylate and vinyl carboxylic acid is used, the β-carboxyethylacrylate comprises at least 10% by weight of said polymer, and C is a water-dispersible macromolecular monomer which has the formula X-Y-Z, wherein X is a moiety copolymerizable with A and B, Y is a divalent linking group which joins X to Z, and Z is a water-dispersible group which contains at least two units which are essentially unreactive under the free radical initiated copolymerization conditions used to form the polymer, and wherein C comprises from 10 to 30% by weight of said polymer; and less than about 0.1 parts plasticizer per part of said polymer.

9. The indicator of claim 1, wherein said indicator is capable of maintaining a wrapped bundle of articles in a closed position during sterilization and normal pre- and post-sterilization handling.

10. The indicator of claim 1, wherein said pressure sensitive adhesive exhibits sufficient adhesion to maintain the wrapped bundle of articles in the closed position during sterilization and normal pre- and post-sterilization handling.

11. The indicator of claim 1, wherein said backing strips exhibit sufficient strength that they will not tear during sterilization and normal pre- and post-sterilization handling.

12. The indicator of claim 1, wherein each of said backing strips is perforated at or near the end to which said sterilization indicator strip is affixed.

13. A sterilization indicator, comprising:

a backing strip having ends and opposing sides and a moisture-resistant, water-dispersible, pressure sensitive adhesive on at least one of said opposing sides; and a sterilization indicator strip affixed to an end of said backing strip such that said sterilization indicator strip is easily removable from said backing strip prior to laundering and said sterilization indicator strip comprises an indicator ink in combination with a backing, wherein said indicator ink is capable of undergoing a color change when exposed to sterilization conditions.

14. A sterilization indicator comprising:

a backing strip having ends and opposing sides and a moisture-resistant, water-dispersible, pressure sensitive adhesive on at least one of said opposing sides, a first portion of the backing strip having one or more apertures; and a sterilization indicator strip affixed to the first portion of the backing strip such that said sterilization indicator strip is viewable through said one or more apertures and said sterilization indicator strip comprises an indicator ink in combination with a backing, wherein said indicator ink is capable of undergoing a color change when exposed to sterilization conditions, and wherein the first portion of the backing strip is easily removable, prior to laundering, from a portion of the backing strip not affixed to the sterilization indicator strip.

* * * * *